US006875429B1

(12) United States Patent
Rudland et al.

(10) Patent No.: US 6,875,429 B1
(45) Date of Patent: Apr. 5, 2005

(54) METASTASIS INDUCING DNA'S

(75) Inventors: Philip S Rudland, Liverpool (GB); Roger B Barraclough, Liverpool (GB)

(73) Assignee: University of Liverpool, Liverpool (GB)

(*) Notice: Subject to any disclaimer, the term of this patent is extended or adjusted under 35 U.S.C. 154(b) by 0 days.

(21) Appl. No.: 09/101,423

(22) PCT Filed: Jan. 10, 1997

(86) PCT No.: PCT/GB97/00074
§ 371 (c)(1),
(2), (4) Date: Nov. 27, 1998

(87) PCT Pub. No.: WO97/25443
PCT Pub. Date: Jul. 17, 1997

(30) Foreign Application Priority Data

Jan. 10, 1996 (GB) .............................. 9600470

(51) Int. Cl.[7] .................. A61K 35/00; C12N 15/63; C12N 5/00; C07H 21/04

(52) U.S. Cl. .................. 424/93.2; 435/325; 435/320.1; 536/24.1; 424/573

(58) Field of Search ............................. 424/93.2, 573; 435/320.1, 325; 455/455; 536/24.3, 24.1, 24.5

(56) References Cited

PUBLICATIONS

B. R. Davies et al., Cancer Research, "Induction of Metastatic ability in a stably diploid benign rat mammary epithelial cell line by transfection with DNA from human malignant breast carcinoma cell lines," May 1994, 54: 2785–2793.*
M. Ilyas et al., European Journal of Caner, "Genetic Pathways in Colorectal and othe cancers," 1999, vol. 35, No. 14, pp. 1986–2002.*
Y. Rojanasakul, Elsevier, "Antisene oligonucleotide therapeutics: drug delivery and targeting," Advanced Drug Delivery Reviews 18 (1996) 115–131.*
J. Holt, Mol. Med. Today, "Antisense therapeutics," May 1996, 2:184–185.*
M. I. Sherman, Annals New York Academy of Sciences, "Antisense and Antiviral Therapy," 1990, 616:201–204.*
Majello et al., "Constitutive and IL–6–induced nuclear factors that interact with the human C–reactive protein promoter", The EMBO Journal, vol. 9, No. 2, pp. 457–465, 1990.
Van de Wetering et al., "Identification and cloning of TCF–1, a T lymphocyte–specific transcription factor containing a sequence–specific HMG box", The EMBO Journal, vol. 10, No. 1, pp. 123–132, 1991.

Lobanenkov et al., "A novel sequence–specific DNA binding protein which interacts with three regularly spaced direct repeats of the CCCTC–motif in the 5'–flanking sequence of the chicken c–myc gene", CTCF: A Novel Factor Binding To MYC Promotor, Oncogene (1990), 5, 1743–1753.
Means et al., "Transcription Initian from the Dihydrofolate Reductase Promoter Is Positioned by HIP1 Binding at the Initian Site", Molecular and Cellular Biology, Feb. 1990, pp. 653–661, vol. 10, No. 2.
Campbell et al., "Comparison of the whey acidic protein genes of the rat and mouse", Nucleic Acids Research, vol. 12, No. 22, 1984, pp. 8685–8697.
Wang et al., "Molecular structure of a left–handed double helical DNA fragment at atomic resolution", Nature vol. 282, Dec. 13, 1979, pp. 680–686.
Gan Wang, Dan D. Levy, Michael M. Seidman, and Peter M. Glaser; Targeted Mutagenesis in Mammalian Cells Mediated by Intracellular Triple Helix Formation; Molecular And Cellular Biology, Mar. 1995, p. 1759–1768; Copyrighted 1995, American Society For Microbiology.
Guang–Chou Tut, Qing–Na Cao, and Yedy Israel; Inhibition of Gene Expression by Triple Helix Formation In Hepatoma Cells; The Journal Of Biological Chemistry; vol. 270, No. 47, Issue of Nov. 24, pp. 28402–28407, 1995; Copyrighted 1995 by The American Society For Biochemistry And Molecular Biology, Inc.
Thomas P. Shields and Jacqueline K. Barton; Sequence–Selective DNA Recognition and Photocleavage: A Comparison of Enantiomers of RH9EN) $_2$PHI$^{3+}$; Biochemistry 1995, 34, 15037–15048; Copyrighted 1995 American Chemical Society.
Stefanic A. Kane, Sidney M. Hecht, Jian–Sheng Sun, Therese Garestier, and Claude Helene; Specific Cleavage of a DNA Triple Helix by FG$^{3:}$ Bleomycin; Biochemistry 1995, 34, 16715–16724; Copyright 1995 American Chemical Society.
Kevin J. Scanlon, Yukinora Ohta, Hironori Ishida, Hiroshi Kijima. Tsukasa Ohkawa, Anna Kaminski, Jerry Tsai, George Horng, And Mohammed Kashani–Sabct; Oligonucleotide Mediated Modulation of Mammalian Gene Expression; p. 1288–1296; The FASEB Journal, vol. 9, Oct. 1995.

(Continued)

Primary Examiner—Ram R. Shukla
(74) Attorney, Agent, or Firm—Brooks Kushman P.C.

(57) ABSTRACT

The invention relates to metastasis inducing DNA's, a method of identifying such DNA's and their use in diagnosis and therapy. It includes a method of screening and recovering met-DNA comprising the steps of: (i) transferring fragments of human DNA from malignant, metastatic cancer cells into a cell line that produces only benign, non-metastasizing tumors when injected into a syngeneic animal; (ii) injecting the transformed cells into the syngenic animal; (iii) selecting those animals in which metastasizing tumors have been identified; and (iv) recovering the met-DNA therefrom.

8 Claims, 6 Drawing Sheets

OTHER PUBLICATIONS

Figure 1:
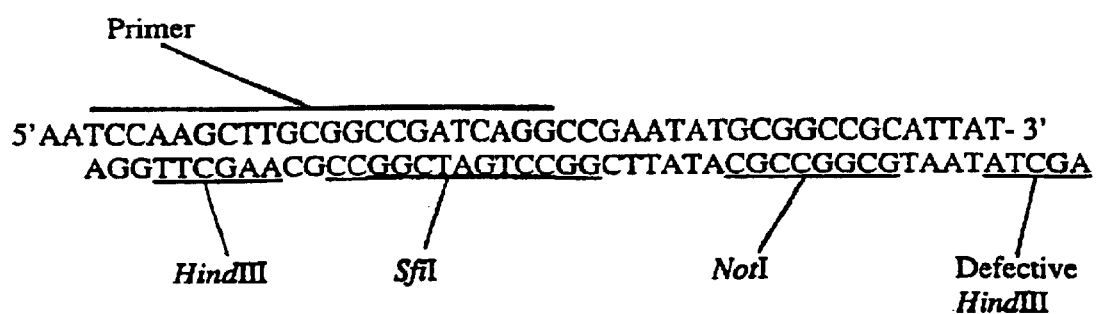

K. H. Vousden, S. A. Eccles, H. Purview and C. J. Marshall; Enhanced Spontaneous Metastasis of Mouse Carcinoma Cells Transfected with an Activated C–HA–RAS–1 Gene; Int. J. Cancer: 37, 425–433 (1986); Copyright 1986, Alan R. Liss, Inc.

Adriana Radler–Pohl, Jens Pohl and Volker Schirrmacher; Selective Enhancement of Metastatic Capacity in Mouse Bladder Carcinoma Cells After Transfection with DNA from Liver Metastases of Human Colon Carcinoma; Int. J. Cancer: 41, 840–846 (1988) ; Copyright 1998 Alan R. Liss, Inc.

U.P. Thorgeirsson, T. Turpeenniemi–Hujanen, J.E. Willilams, E.H. Westin, C.A. Heilman, J.E. Talmadge, and L.A. Liotta; NIH/3T3 Cells Transfected with Human Tumor DNA Containing Activaged RAS Oncogenes Express the Metastatic Phenotype in Nude Mice; Molecular And Cellular Biology, Jan. 1985, p. 259–262; Copyright 1985, American Society For Microbiology.

* cited by examiner

SEQUENCE LISTING

<160> NUMBER OF SEQ ID NOS: 8

<210> SEQ ID NO 1
<211> LENGTH: 1033 base pairs
<212> TYPE: DNA
<213> ORGANISM: Homo sapiens -continued

<400> SEQUENCE: 1

| | | |
|---|---|---|
| cttccttggt gctctatgtc ttgcctctcc ccttctccag tcccattaag ccataaccat | 60 |
| cttgacagac tctgggacag tcccctctgc tctcctgttg gcgcctgagt cccttttgc | 120 |
| ctgaggaccc ttcacgtagc ctcccatctg gatgacctag tagaagacgt gggaagttgt | 180 |
| cacactcagg taactgagca gagctcgagg atttaaagtg agtctgggga gcctcgagga | 240 |
| ttgatctgct gccttaaaaa gccaattgga tgactaaccc agactattgt cactttaggt | 300 |
| gggaagtcac tagcatatct gatgggtcac atctgagaaa ggtttctagc agtggtggcc | 360 |
| ttgtgtgagc agcatggcgt gtatcatggt gtgcagcata ctcaggctgc ttgcaacact | 420 |
| cgaggctctt cttcagtatt aggggaacca ctggtgttga acatggtcca agaatacagt | 480 |
| catgtgagga gaatcccaat gcgtcaggag aaaacgagag tctgtgacct ccattcttca | 540 |
| agatacagaa ttattcttgg actgtgtttt catgctcctt gtggatggga gtgagtttac | 600 |
| ttcaggttaa tcagcattgc ttactgttgg tattcaagta aatgcttaaa ttatcctgga | 660 |
| tatacctctg tgggaagcag gttttttgata catgcagctt gtccttgtga ttgatactgc | 720 |
| ttgaactcaa gagaactttg ctcatgtgat ctttcttaac cgatggagta gaaactgtct | 780 |
| gatgctctca ataaagttgg ctcttgcacg agacgttagt ctgtcctgtt tatctgctcc | 840 |
| attcttccgc tcccacggcc tctacagcac taaacccacc accgatagac tcagtctttc | 900 |
| actgacaaac atcaccagag gctcttaact gagattataa actgttacta gatgatgggt | 960 |
| tgaatcgctc cccagaaaca taaacattta cttggagaac tcaagacccc tttgtagaca | 1020 |
| taactcccat ggt | 1033 |

<210> SEQ ID NO 2
<211> LENGTH: 1058 base pairs
<212> TYPE: DNA
<213> ORGANISM: Homo sapiens

<400> SEQUENCE: 2

| | | |
|---|---|---|
| attgctgtga gcctattagc gacatttggt gacgcccctt ttaaggggt agatacaaag | 60 |
| aatgggttga aattctgtgc cacaaacgct ctccatgttt tcacaattac acttgcaacc | 120 |
| tgtggtcagc agccagaatt tagggatgtg atgggacagg gtcggggaaa gaaggagaag | 180 |
| ggtaaaggaa agacagcacg ttaaagtcca acagctcca ggagactatc tgtagaaata | 240 |
| acatcagacc atgaggagaa ttgatatcat tgttttcaa tgggtatcgc caagggaact | 300 |
| ttccatctga ttaaaaataa ttactgctgg cactaaatcc aattggaaat gccccacaca | 360 |
| atttatcttc cacttcatgc tgctaccata tgcctgacgt ggcggagcag aagcattccc | 420 |
| tcccgttctg ataaatagta ctttgtaaat atttggagac gggagctctg gtgacaggga | 480 |
| acacgtacaa accggcctgt ttatcatgtt cccgatagag gccctctttg acgtacagga | 540 |
| ccccaaaaca gtcaggatgc tgtgaatttc cttccatgaa gccttgttca caattagcaa | 600 |
| ccattggagg aagcaggctg cactgtctac acaagtggc actttccaaa gagcacacat | 660 |
| atattggagc aagacatttt gctggctgac tggtgctgtg taagctgata aactgctata | 720 |
| tttattaaac tggcttttct ttgaacaccc cactcaagga aaaaaaaca cacttagggt | 780 |
| gacattattt ggagatgaag tctttataga gatgcttaag tttaaacgag acttttaaag | 840 |
| ccggctctat tccatttaat gaatggtgtc cctacaaagg aagaaactgg acagaggta | 900 |
| tgtacacttg tgtgtgtgtg agagacaacg tgaggagctg aagaggagca cgtacaagtc | 960 |

```
agagaaaggc tgacccttat tcacactgag caaaccagtc atgtgtgggt cgatagatga    1020
gagtatcccc caagactcac acattcgaac gcttggtc                           1058

<210> SEQ ID NO 3
<211> LENGTH: 1008 base pairs
<212> TYPE: DNA
<213> ORGANISM: Homo sapiens

<400> SEQUENCE: 3
aggaccagag ttcacatccc atcaaatggc ccagaaggtt ttaatgctgt cttttggccc     60
aggggcgaac tgcacacaca tgtgcacata cacttacaga gacacacatt cagcagcata   120
agaacacaat cacaaataaa aaaaatcttg aaaaatttta agctaaaatt gttaagaaat   180
aacatatata caatttttct ttatttttt aaagatttat ttatttaatg tatatgagta    240
cactgcctct ccctccagac atagcagtac agggcatcgg atcccattac agatggttgt   300
gagccaccat gtggtttcac agatggttgt gagccaccat gtggtttcag gaattgaact   360
caggaccttt ggaagagcag tcagtgctct taacctctaa gccatctctc ctgaccctta   420
tatacaattt taatgctacg tacacacaac ttctcttcc tttaatggtt gagattttg     480
tctggagaag taagaataaa ggagggaaag acattgctt tcacattgca ccagtgggaa    540
cagcgtgttt aaagtaggaa tgccatgaaa tgactggcct gccttctcat tactgttcct   600
cccactcctc cttttaactg gagctccttt atctaattta ttagtttgac gatacccagg   660
gttttcttct gttttgatct ttttaagaca gagactcacc atatagccct ggctggcctg   720
aagctcacta tgtagaccag tctggccttg aactcaaagg agatctatct gcttcctagt   780
gctgggatta aaggcttgtg ctaccaagtc tggtctgagg cttggagca gcctcggttt    840
tggccttctt taaggatctc taagctagca gtaagtagcc tagccatgct gttgtaggaa   900
gttgttcgtt catcctggct ccagcacaaa ggcagtcact aaacgtcggc ctcatttcat   960
cagagctgaa tgcaaattcc ttgtgctctt cctgtgtcct cctggaac               1008

<210> SEQ ID NO 4
<211> LENGTH: 1088 base pairs
<212> TYPE: DNA
<213> ORGANISM: Homo sapiens

<400> SEQUENCE: 4
agttggggac acagcttgct tgattaagat gtttcttggg aaaaggagtt aagcctaatg     60
atttccaatg gaaaggactg ctaattgggg aggcaatgtt gcttaattgg gacacctgcg   120
ggtaattaaa agctctctcc cagtggcctt tcctgttttt ggctctggga ggcgaaggca   180
ttgagaggga tgcaggcatt ctaagggctg gttcttggtt tctcccttcc cctctgtcca   240
aactcagtga ggtatccctg tctgtgctgt ccttagagtg ccgtcctgag gccttggtga   300
gttaaggtct ctggatctga gctgcctcag ggaaacgcat gagctcattg gaaaggggag   360
aaccaggcaa aggtgttggc tgtgacctca gaattctgag gggcaaaggt tcaaggctaa   420
ctctcattat agagcaagtt tgagactggc tgggaacaa aaatataaag tgagtgaggt    480
catatgacag cacctgagga gtcctgtccc tagagatcat aaggacctgg ctgctgggga   540
cttgttgcag atggcacttt tgtcgagag agggacctg ccccagcatg ggaggccctg     600
gaagatcctc tggattaact gtgaacactg attgctgctt tatacctgga gttgtgctgt   660
tatctggtac acatctgctg ggtgaatgag ttcatgggct ttatttcagt gaggtattta   720
cctgaggaga aagaaggact ggtgccacaa agcacagctt ttaaatctgt gggttgtgac   780
```

```
ccattatgga ctatcataac tgagtgcagg tatcaagaat actttagcag gtggtaaaaa      840 gattttttgaa tgcgcaacga ccaaaactga actcaaaaat caagcatggc atggatcctg    900
ggtgctcctg gaagcacttg cctttactgc attgtgcgac ttgacggtag ccttggttct    960
gaatgcacaa cacgtgggct ttgggctgca caggccacca cgccgtgcct gaaacacctc    1020
agctcaggtt tgtggctatg tcctatgact tggacttact tttattgcac atataaatat    1080
tttcctgc                                                              1088

<210> SEQ ID NO 5
<211> LENGTH: 960 base pairs
<212> TYPE: DNA
<213> ORGANISM: Homo sapiens

<400> SEQUENCE: 5 gaggggggtgg tggcacagtt atgttttttgt aggaagggtt ccatgaacct cagcagagct     60
cgggttagaa atttaaaagc cctgagggga attttttttt taaatcgcta tgaatctgac    120
atgagaaaaa cagatcagaa acgttcttgt gcttcagaaa aggacaagtg tgtgagctaa    180
cagactgcac actggtgttc gaggcacatc tggatcacag gagcgtcaga taatgtcccc    240
aaaggtaaat gcatttgctt gcacagtacc gagtgtggtg gggggtgcct acagcccagc    300
ggttctcaac cttcctgatg cttcgaccct ttaatacagt gcctcatgct ctggtgacct    360 cccccaacctt aaaattattt ttgttgctgt tcataactgt gattttgata ctgttatgaa    420
ttgtaatata ataatttttg aagaaagagg tttgccaagg gtttgagaac tgctgttcta    480
gccccacgtg gatggttttt cgtcatttgg ggtttttatg aggcagagtc ttatgtagcc    540
caggctagca gcctagaatg tgctacttag ctgaggaata accttggaac ttctgaggac    600
tggagagact ggcttagtcc tcaagaaact ggaaatagct ggagtttggc tacttgtggg    660
ttcctttttc ttcaaacctt ttctactctt tttccaccct gtcggccccc taacactaaa    720
taagaaagag aaaggggagc atagagggga aaagaaaccc ctgaataacg tcagtagttg    780
gcaaaggggg gtgacatatg ttgtcattag accacatcct ggtgattaag gggagtcaag    840
ttccttgggg caagtttgat ctttcgtgta acgatatcta atttcttctc cctgttgctt    900
cgtctttgtg aacaacgact tgataaccca caatggacca tcaaccaacc aaccaaccat    960

<210> SEQ ID NO 6
<211> LENGTH: 1090 base pairs
<212> TYPE: DNA
<213> ORGANISM: Homo sapiens

<400> SEQUENCE: 6
ttgtctctgg tgttacttgt ttttcccattt ctgacagtgg tttgaccttc tatacgcctg     60
tgtgtcagga gtgctgtaga cctatttttcc tgttttcttt cagccagtta caggaacaga    120
gtgttctact gtcagatgtg tagctgttcc tgtccactga ctttcaagct gtctctgtgt    180
gcaggaacca gaagggcctg tccctacttc tactgggccc ctacgcacag ggggcctaga    240
tggtgctagg tgttttcctc tagagcctga aatgtgggca gagagtagtc tcctctggtt    300
tcctaggtat gtcttcccct ctgaaggtct agctctccct tccatgggat atgggtgcag    360
ggagctgttt gaccaggtcc tctcaaatcc gggtgcagtc tggaccgcag gctcctgtag    420
cttgcctgct gcaatcttcc cgcacccaga ggcacccaag tttcctcttg gccaaggat    480 gtgggcaaag gtgggcagaa gtggcaatct ctcctgccct agcgtctcag gattgccctc    540
```

-continued

```
acttctgggc aatccgctct ctcttccaca gggtttggga gcagggagct gtgggccggt      600
atcaggcaaa ggtttgaggc aaccagttag aaactggaag tgtcaggtcc cagaggaatt      660
ttgcctttgt gtgtcctgag tccaccaggc aggtcacttg gagcagaaaa attggttttc      720
ccctcggtct caggcctgaa gttgcacctc agggttggct ttcagctgta cctgtggaaa      780
gtatggtttt aaaaatctaa gatagctatc atgcagcaag gcttgtgtaa aatgtctatt      840 tggttcctttt atgacttact tttgctgtac tgaggatcaa acctagggtc tcaagcagtc     900
atcacaattc tctgtcactg atccagctcc atttctattt tcttttgtcc cgcgcgatct      960
ctcgccagca agaaaacacg ctagggacat acgaatcctt gctgcagcca aaactttat     1020 tgaatcttaa ggagaagccc gcgcaccgga ctggcgcggt ttatatacac cctagcacag    1080
tgcatccaca                                                           1090
```

<210> SEQ ID NO 7
<211> LENGTH: 45 base pairs
<212> TYPE: DNA
<213> ORGANISM: Homo sapiens

<400> SEQUENCE: 7

```
aatccaagct tgcggccgat caggccgaat atgcggccgc attat               45
```

<210> SEQ ID NO 8
<211> LENGTH: 47 base pairs
<212> TYPE: DNA
<213> ORGANISM: Homo sapiens

<400> SEQUENCE: 8

```
agctataatg cggccgcata ttcggcctga tcggccgcaa gcttgga             47
```

METASTASIS INDUCING DNA'S

BACKGROUND OF THE INVENTION

1. Field of the Invention

The present invention relates to metastasis inducing DNA's, a method of identifying such DNA's, and their use in diagnosis and therapy.

2. Description of Related Art

Most cancers are thought to be due to alterations in specific genes caused either by mutation making their gene-product in some way more effective or by over expression of a normal gene giving an enhanced effect. These oncogenes have largely been identified by introducing gene-length fragments of DNA from human cancers into a mouse fibroblast cell line, in culture, and selecting those cell lines that grow in an uncontrolled manner in liquid or semi-solid medium. The oncogenes themselves have been isolated by cloning the human DNA fragments away from the mouse DNA by standard recombinatorial techniques. Alternatively mutations can arise in genes that suppress their own activity such as, for example, p53 or Rb or which suppress the levels of their products such as, for example NM-23. These are referred to as tumour suppressor oncogenes. In the commonly-occurring cancers, it is believed that between 5 and 7 such changes in oncogenes or tumour suppressor oncogenes are required to produce a full-blown cancer.

WO 86/03226 discloses a method for detecting a discrete, transmissible mammalian gene associated with tumour metastasis. The method uses a non-syngeneic system. The teaching was later retracted—Proc Nat. Acad. Sci USA, 1988, 85 5581.

WO 94/28129 identifies a tumour metastasis gene of 2858 base pairs which codes for a protein which is expressed in malignant human tumours and their metastasis. The method used to identify it used a non-syngeneic system employing nude (defective) mice.

Cancer research 54, 2785–2793 (1994) is a paper by the applicants. It discloses a method for showing the presence of metastasis inducing DNA. No disclosure is, however, made of how to recover the sequences for identification.

Cancer research 54 832–837 (1994) is a paper suggesting that antisense OPN DNA expression was associated with reduced tumorigenicity of these cells in the flanks and in lungs. The paper does not measure or investigate metastasis as such.

EP 0607054 disclosures a process for constructing a cDNA library. It described a method, using linkers and PCR for identifying signal peptides. The application is not to metastasis at all and the approach uses expression vectors for detection.

The major forms of cancer, including breast cancer, lung cancer and colonic cancer cannot be cured effectively because, although the current therapies may be effective against the primary tumours, they are largely ineffective against the disseminating or metastasizing cells, which ultimately kill the patient. Despite the enormous effort in cancer research very little is known at the molecular level about the most important life-threatening process, that of metastasis. Most of the oncogenes and suppressor oncogenes that have been discovered have been found from their ability to promote uncontrolled growth of the mouse fibroblast cell line. The major problem in this field is that determining cell growth does not give a measure of the process of metastasis. In fact, although uncontrolled growth is an important aspect of the initial events in the development of a cancer, the rate of growth of distant metastases can be remarkably slow. Hence the process of metastasis is largely independent of processes involving cell-growth, except in its final phases. Therefore, it is unlikely that oncogenes and tumour suppressor oncogenes will have much involvement in the process of metastasis and be useful diagnostic or therapeutic targets for control and elimination of metastatic disease.

SUMMARY OF THE INVENTION

It is one object of the present invention to identify DNA comprising, consisting of or containing sequences involved in metastasis, hereinafter referred to as metastasis inducing DNA's -or Met-DNA's for short.

According to a first aspect of the present invention there is provided a method of screening and recovering a regulatory DNA capable of inducing metastasis comprising the steps of:

i. transferring tagged fragments of a human DNA from malignant, metastatic cancer cells into a cell line that produces only benign, non-metastasizing tumours when injected into a syngeneic animal;

ii. injecting the transformed cells into the syngeneic animal;

iii. selecting those animals in which metastasizing tumours have been identified; and iv. recovering the regulatory DNA capable of inducing metastasis therefrom.

Preferably the DNA fragments transferred in step 1 are fragments of from 0.1 to 50 kilo base-pairs, more preferably 0.5 to 50 kilo base-pairs.

Preferably the cell line that produces only benign non-metastasizing tumours when injected into a syngeneic animal is a rat mammary epithelial cell line, such as, for example Rama 37.

Preferably the fragments of human DNA from malignant, metastatic cancer cells are tagged to assist in their removal or insertion from or into a host or vector, such as, for example, the oligonucleotide tag illustrated in FIG. 1. This tagging procedure overcomes the problem of identifying the inserted human DNA sequences in the rat genome of the transfected rat cells. Human-specific repetitive DNA (Alu) sequences are spaced sufficiently in the human genome that in many human DNA fragments of this size they will be absent.

DETAILED DESCRIPTION OF THE INVENTION

In one embodiment, fragments of human DNA from malignant, metastatic breast cancer cells are introduced into a rat mammary epithelial cell line Rama 37 which produces only benign, nonmetastasizing tumours when injected into syngeneic rats.

By way of example only, the transfer of restriction-enzyme HindIII-fragmented DNA from malignant metastatic rat and human breast cancer cell lines into a benign Rama 37 cell line produced a small proportion (1–3%) of transformants which, when reintroduced into the syngeneic rats, caused these cells to metastasise, principally to the local lymph nodes and lungs. In contrast, fragmented DNA from nonmetastatic cells and the standard oncogenes (Ha-ras, Middle T Antigen gene, and Large T Antigen gene) produced no metastasizing transformants. The latter result confirms the non involvement of such oncogenes in the metastatic process per se. However, the fact that metastasis can be transferred in a genetically dominant manner suggests that other dominantly-acting DNA fragments are largely responsible for this process. The full results of the above experiments are shown in table 1, which shows the incidence of tumours and metastases for Rama 37 transfected cell lines.

TABLE 1

| Donor DNA | Cells injected | No. Rats | Tumours | % | Metastasis | % |
|---|---|---|---|---|---|---|
| None | Rama 37 | 46 | 22 | 48% | 0 | 0% |
| Human metastatic | R37-Ca2-LT1 | 20 | 18 | 90% | 6[b] | 33% |
| Human benign | B-T1 | 18 | 18 | 100% | 0 | 0% |
| Human/rat metastatic tagged | R37-Ca2-HT | 37 | 29 | 78% | 6[b] | 21% |
| Human/rat metastatic | R37-Ca2-H | 31 | 24 | 77% | 4[b] | 17% |
| Human/rat benign tagged | R37-B-HT | 39 | 31 | 79% | 0 | 0% |
| PCR fragment F1 | R37-F1 | 30 | 28 | 93% | 12[b] | 43% |
| PCR fragment F2 | R37-F2 | 40 | 36 | 90% | 9[b] | 25% |

The column headed "cells injected" gives the cell type in short hand, and full details are given below:

Rama 37 are Rat mammary 37 benign cells; R37-Ca2-LT1 is a cell line from a lung metastasis of Rama 37 cells transfected with fragmented DNA from the metastatic breast carcinoma cell line Ca2-83 (Cancer Res 54 2785–2795, 1994); B-T1 is a cell line from a primary tumour of Rama 37 cells transfected with fragmented DNA from the benign breast cell line HMT-3522 (Cancer Res. 54 2785–2795, 1994); R37-Ca2-HT is a cell line of Rama 37 cells transfected with tagged DNA fragments from metastatic transformant R37-Ca2-LT1; R37-Ca2-H is a cell line of Rama 37 cells transfected with untagged DNA fragments from metastatic transformant R37-Ca2-LT1; R37-B-HT is a cell line of Rama 37 cells transfected with tagged DNA fragments from the benign transformant B-T1 as a control; R37-F1 is a cell line of Rama 37 transfected with PCR fragment F1 from a cell line of a lung metastasis of R37-Ca2-HT; and R37-F2 is a cell line of Rama 37 transfected with PCR fragment F2 from the same cell line of a lung metastasis of R37-Ca2-HT.

The b annotation in the column headed metastases identifies the transfecting DNA's giving rise to significantly more metastasis than Rama 37 cells (P<0.05, Fisher exact test). The animals were autopsied after 3 months.

Figure 2:
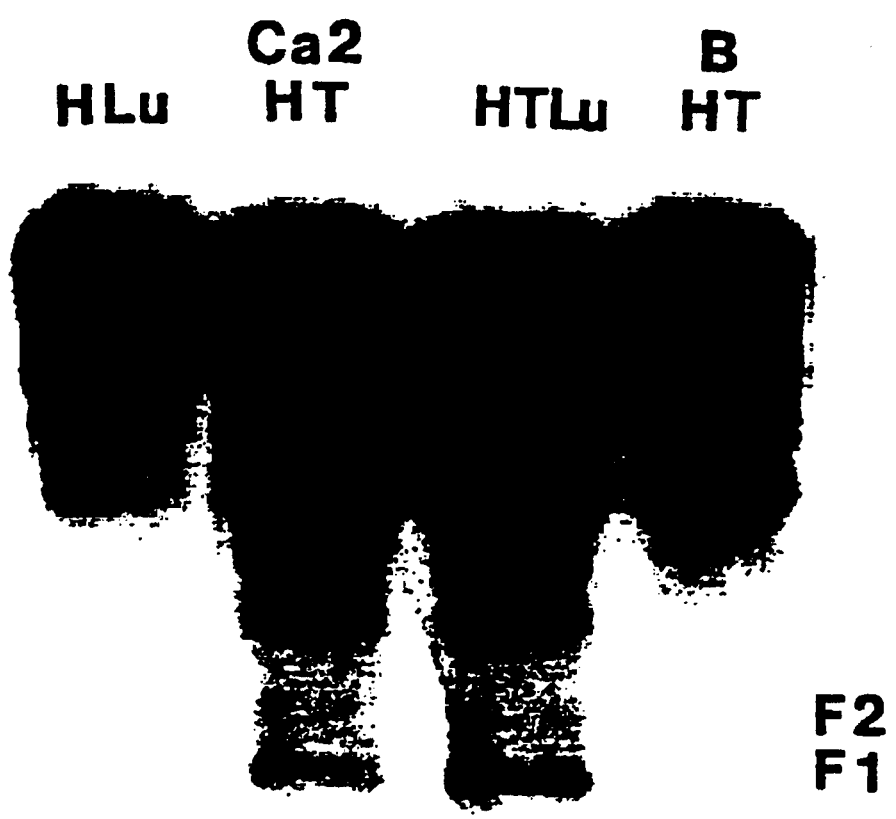
Figure 3:
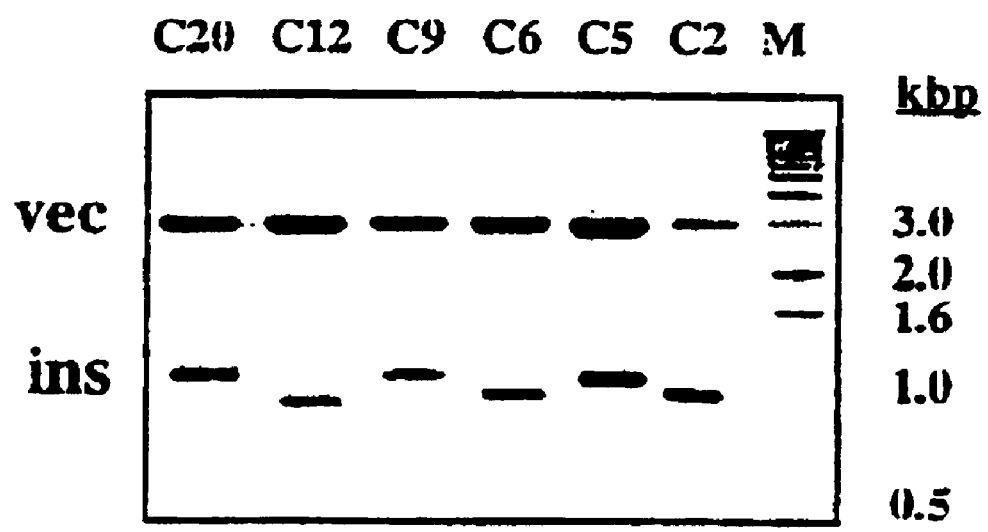

To aid the rescue of metastasis-inducing human DNA sequences from the rat transformant cell lines, all the HindIII-fragmented DNA's from one such metastatic transformant, R37-Ca2-LT1 (Table 1) were tagged at both ends with double-stranded synthetic oligonucleotides that provide restriction enzyme and unique PCR primer sites. (SEQ. ID. Nos: 7 and 8.) These are shown in FIG. 1 The tagged DNA fragments include 4 restriction sites: SfiI and NotI, a defective HindIII site at the 3' end for linking to the HindIII sites at the ends of the human DNA fragments, thereby destroying it, and an internal HindIII site located near to the 5' end, which when cut after ligation generated new fragments with HindIII ends. The fragments were transfected into the parental Rama 37 cells, and after transfer of the cells to the mammary glands of syngeneic rats, metastatic cell lines were isolated from the resultant rat lung metastases. The tagged, fragmented DNA incorporated into the metastatic transfacted Rama 37 cell lines was directly amplified between the tags by PCR and yielded bands at about 1300 to 1500 bp that were responsible for the metastasizing ability of the transfected cells. These results are shown in FIG. 2 which shows the DNA fragments produced by PCR of metastatic transformants. Two new cell lines, established from the culture of lung metastases of R37-Ca2-HT (tagged, metastatic DNA transformant) and R37-Ca2-H (untagged, metastatic DNA transformant) (see Table 1) in rats were termed HTLu and Hlu, respectively. They were run against the tagged benign transformant cell line R37-B-HT and the tagged metastatic transformant R37-Ca2HT. Cellular DNA was amplified by PCR using a short oligonucleotide primer of 22 bp from positions 3–24 of the tag sequence as shown in FIG. 1. Compared with the control DNA's from Hlu and B-HT cells, two extra bands, F1 and F2, of about 1300 bp and 1500 bp respectively, were specifically amplified from genomic DNA of the Ca2-HT and HTLu cells when PCRed DNA samples were run on 0.8% agarose gels containing ethidium bromide and photographed in U.V. light. The fluorescent bands of DNA are shown in negative imaging for clarity. Cloning of these pooled DNA's yielded six independent fragments and the results are illustrated in FIG. 3. FIG. 3 shows pBluescript clones of metastatic DNA fragments F1 plus F2. The two broad PCR DNA fragments F1 and F2 were excised from the gel in FIG. 2, combined, and cloned directly using the AT procedure into a suitably modified pBluescript vector and the clones of recombinant vectors were cut with HindIII to excise the cloned fragments. These cut recombinant vectors were analysed on a 0.8% agarose gel containing ethidium bromide and photographed in U.V. light. The sequences of some clones eg. C10 and C9-DNA's were identical; the six independent sequences arose from clones numbered C2, C5, C6, C9, C12 and C20 and hence are referred to as C2-DNA, C5-DNA etc as shown in FIG. 3. The position of the vector (Vec) DNA and insert (Ins) DNA are indicated and a standard molecular weight ladder in kilobase pairs (kbp) is shown in lane M. Transfection of these cloned DNA fragments singly into the parental benign cell line confirmed that all fragments (C2, C5, C6, C9, C12 and C20-DNA's) produce metastases. These are shown in Table 2 which tabulates the incidence of tumours and metastases for Rama 37 cells transfected with cloned Met-DNA's. The superscript a–e indicate:

[a]Benign nonmetastatic Rama 37 cells were transfected with pSVneo or with pSV2neo and different independently-cloned inserts of the pBluescript library of pooled F1- and F2-DNAs termed C2-DNA etc. or with a cylomegalovirus expression vector pBKCMV (CMV-1) or with the CDNA for osteopontin (opn) cloned into the same expression vector pBKCMVopn (OPN-1).

[b]Transfectants were tested for their level of opn mRNA relative to that in Rama 37 cells by Northern hybridisations to opn CDNA using a Shimadzu CS9000 scanning densitomer. RNA loading levels were standardised with respect to a 36B4 ribosomal protein constitutive probe.

[c]Transfectants were tested in the mammary glands of rats for the percentage (%) of tumour-bearing animals with metastases in the lungs after 3 months. The incidence of tumours produced by all transfectants was 100%.

[d]Significantly higher levels than for Rama 37 cells (P<0.05;Mann Whitney U test).

[e]Significantly more metastases than for Rama 37 cells (P<0.05;Fisher exact test).

Thus Koch's postulate has been satisfied for all metastasis-inducing-DNA's (Met-DNA's) in this system.

Southern hybridisations and PCR amplifications have established that the Met-DNA's are specifically present in their respective transformants.

Figure 4:
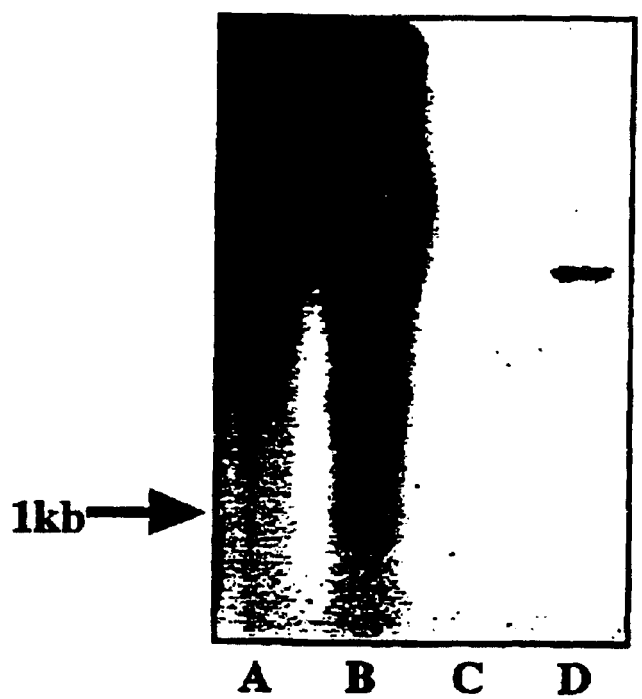
Figure 4:
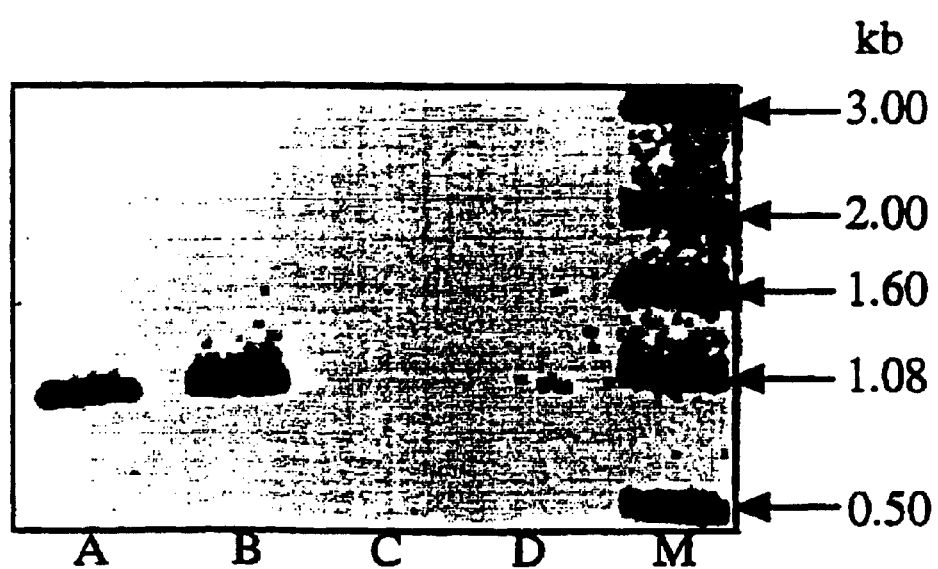
Figure 5A:
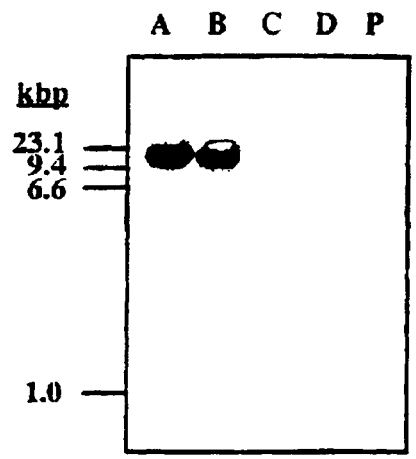
Figure 5B:
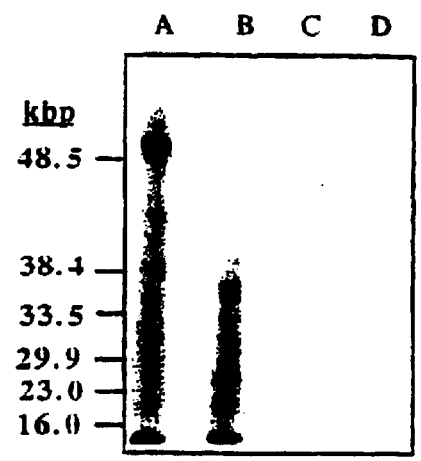
Figure 5C:
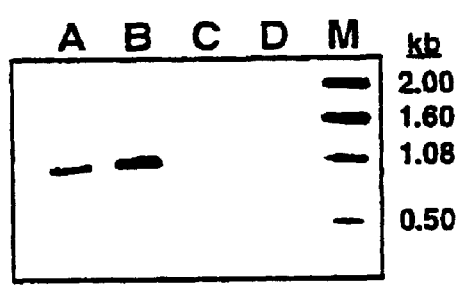
Figure 5D:
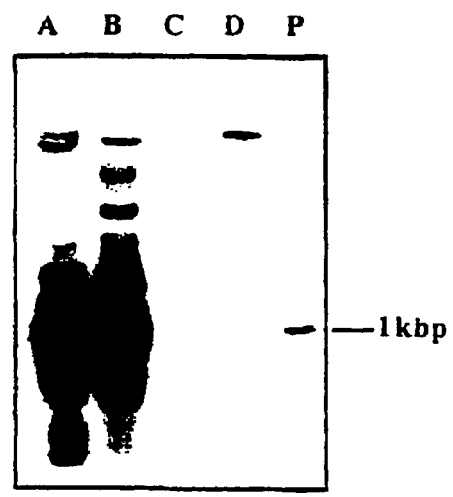

FIG. 4 shows detection of C9-DNA in transformant cell lines. Cellular DNA was isolated from (A) a cell line from a lung metastasis produced by injection of C9-DNA transfected Rama 37 cells in rats; (B) C9-DNA transfected Rama 37 cells (see FIG. 3 and Table 2); (C) benign Rama 37 cells; (D) benign BT-1 cells (see Table 1). These DNA's were digested with HindIII and the digested DNA was analysed on 0.8% agarose gels either by (A) Southern blotting to a probe of [$^{32}$P] radioactively labelled C9-DNA, and the radioactivity visualised on X-ray film or (B) by PCR using the 17 oligonucleotide fragment from either end of the C9-DNA as primers and run with a standard molecular weight marker ladder. The newly synthesised DNA in B is visualised by fluorescence of the ethidium bromide in the gel in U.V. light.

Surprisingly, the sequences of these Met-DNA's (hereafter SEQ. ID. Nos. 1–6), although human in origin, do not correspond to known genes and most do not include any known open reading frames. Furthermore none of these Met-DNA's are expressed as mRNAs in their transformants and hence are not dominantly-acting oncogenes. They therefore contain entirely novel short stretches of regulatory DNA capable of inducing metastasis.

The state of the Met-DNA's has been investigated in the metastasizing transformant cells. Bands of greater than 23 kbp which hybridise to the C9-DNA probe have been obtained from HindIII digested C9-DNA transformants, and pulsed-field gel electrophoresis yields multiple bands of about 16–48 kbp after similar digestions as shown in FIG. 5a–d.

FIG. 5 shows the detection of Met-DNA in transformant cells. The cellular DNA was isolated from :(A) a cell line from a lung metastasis produced by injection into rats of C9-DNA transfected Rama 37 cells; (B) C9-DNA transfected Rama 37 cells; (C) benign Rama 37 cells; (D) benign primary tumours of R37-BT-1 cells. These DNAs were digested with excess HindIII and the digested DNA was analysed on agarose gel (a) with continuous electric field; (b) with a pulsed electric field; or (c) by PCR using 17 mer oligonucleotide primers from each end of the C9-DNA; (d) These DNAs were also digested with excess EcoR1 and analysed on agarose gels with a continuous electric field. The resultant gels were either (a.b.d) Southern blotted to a probe of [$^{32}$P] C9-DNA without tags and the radioactivity visualised on X-ray film or (c) the newly synthesized DNA was visualised by fluorescence of the bound ethidium bromide in U.V. light. Controls with (a) C9 DNA in lane P and (c) standard molecular weight marker ladder in kilobase paris (kbp) in lane M were also run. This result strongly suggests that the flanking HindIII sites have been destroyed by the transfection/integration process. The highest 48 kbp band is preferentially retained by the cell line isolated from a lung metastasis (FIG. 5b); thus is is likely that this represents most of the metastasis-inducing DNA (Table 2). The C9-DNA transfectants contain about 100 copies per haploid genome of C9-DNA when compared with a single copy (FIG. 5a, lane P) 10 copy and a 100 copy DNA control. PCR amplification of the integrated DNA using primers complementary to the cDNA adjacent to the untagged ends of C9-DNA produces a single 1kbp product showing that the integrity between the primer sites has been maintained (FIG. 5c). However, digestion of the DNA of C9-DNA transfectants with EcoR1 (which cuts once internally within the C9-DNA) and hybridisation with a C9-DNA specific probe yields predominantly a 1 kbp band of similar size to the original C9-DNA insert (FIG. 5d). This 1 kbp band probably arises from the digestion of tandem repeats of C9-DNA. Similar results have been obtained with C2, C5, C6, C12 and C20-DNAs.

The occurrence of C9-DNA has been investigated in pilot studies in the DNA of human breast cancers. Hybridisation of C9-DNA occurs to HindIII-digested DNA from 4 out of the 9 breast tumours tested, whereas no hybridisation signal is detected from similarly-digested DNA from normal human breast or colon tissue. In this case a single hybridising band of 1000 bp is detected (FIG. 6).

Figure 6:
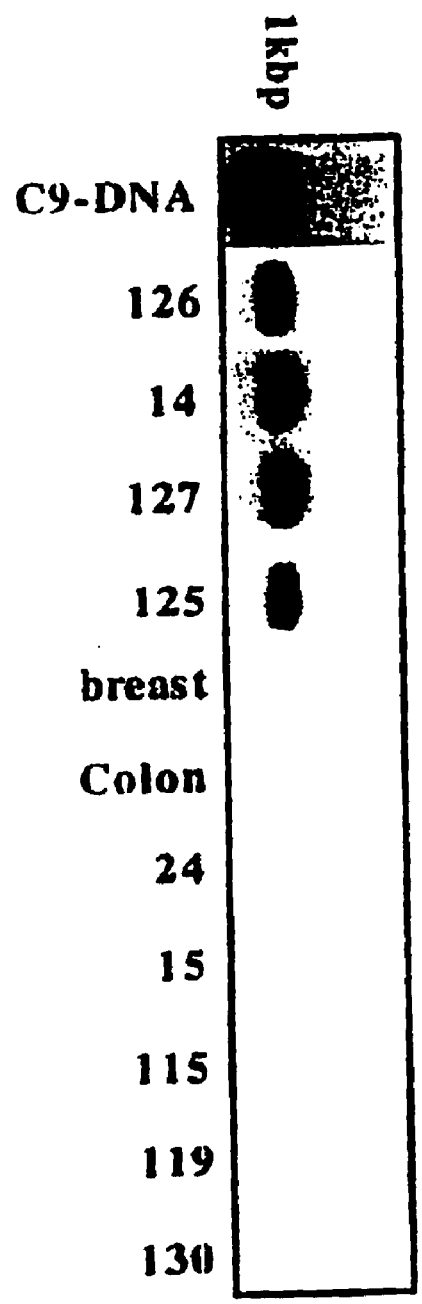

FIG. 6 illustrates detection of C9-DNA in human breast tumours. Cellular DNA was isolated from a selection of nine randomly-picked human breast tumours numbered 14–130 and from normal breast and colon tissue together with C9-DNA as a control. These DNAs were digested with an excess of HindIII and the digested DNA was analysed on agarose gels, Southern blotted on to a filter and hybridised to a probe of [$^{32}$P]C9-DNA without tags and the radioactivity visualised on X-ray film. Similar results have been obtained using PCR for C9-DNA.

According to a second aspect of the present invention there is provided a regulatory DNA capable of inducing metastasis consisting essentially of a human DNA fragment of less than 1.6 kilobase pair in length obtained from a malignant, metastasis cancer cell.

According to a third aspect of the present invention there are provided DNA consisting essentially of a regulatory DNA capable of inducing metastasis from SEQ. ID. NO. 1:

```
CTTCCTTGGT GCTCTATGTC TTGCCTCTCC CCTTCTCCAG TCCCATTAAG CCATAACCAT

CTTGACAGAC TCTGGGACAG TCCCCTCTGC TCTCCTGTTG GCGCCTGAGT CCCTTTTTGC

CTGAGGACCC TTCACGTAGC CTCCCATCTG GATGACCTAG TAGAAGACGT GGGAAGTTGT

CACACTCAGG TAACTGAGCA GAGCTCAGAG ATTTAAAGTG AGTCTGGGGA GCCTCGAGGA

TTGATCTGCT GCCTTAAAAA GCCAATTGGA TGACTAACCC AGACTATTGT CACTTTAGGT

GGGAAGTCAC TAGCATATCT GATGGGTCAC ATCTGAGAAA GGTTTCTAGC AGTGGTGGCC

TTGTGTGAGC AGCATGGCGT GTATCATGGT GTGCAGCATA CTCAGGCTGC TTGCAACACT

CGAGGCTCTT CTTCAGTATT AGGGGAACCA CTGGTGTTSG AACATGGTCC AAGAATACAG
```

-continued

```
TCATGTGAGG AGAATCCCAA TGCGTCAGGA GAAAACGAGA GTCTGTGACC TCCATTCTTC

AAGATACAGA ATTATTCTTG GACTGTGTTT TCATGCTCCT TGTGGATGGG AGTGAGTTTA

CTTCAGGTTA ATCAGCATTG CTTACTGTTG GTATTCAAGT AAATGCTTAA ATTATCCTGG

ATATACCTCT GTGGGAAGCA GGTTTTTGAT ACATGCAGCT TGTCCTTGTG ATTGATACTG

CTTGAACTCA AGAGAACTTT GCTCATGTGA TCTTTCTTAA CCGATGGAGT AGAAACTGTC

TGATGCTCTC AATAAAGTTG GCTCTTGCAC GAGACGTTAG TCTGTCCTGT TTATCTGCTC

CATTCTTCCG CTCCCACGGC CTCTACAGCA CTAAACCCAC CACCGATAGA CTCAGTCTTT

CACTGACAAA CATCACCAGA GGCTCTTAAC TGAGATTATA AACTGTTACT AGATGATGGG

TGGAATCGCT CCCCAGAAAC ATAAACATTT ACTTGGAGAA CTCAAGACCC CTTTGTAGAC

ATAACTCCCA TGGT
```

According to a fourth aspect of the present invention there are provided DNA consisting essentially of a regulatory DNA capable of inducing metastasis from SEQ. ID. No. 2:

```
ATTGCTGTGA GCCTATTAGC GACATTTGGT GACGCCCCTT TTAAGGGGGT AGATACAAAG

AATGGGTTGA AATTCTGTGC CACAAACGCT CTCCATGTTT TCACAATTAC ACTTGCAACC

TGTGGTCAGC AGCCAGAATT TAGGGATGTG ATGGACAGG GTCGGGAAA GAAGGAGAAG

GGTAAAGGAA AGACAGCACG TTAAAGTCCA AACAGCTCCA GGAGACTATC TGTAGAAATA

ACATCAGACC ATGAGGAGAA TTGATATCAT TGTTTTTCAA TGGGTATCGC CAAGGGAACT

TTCCATCTGA TTAAAAATAA TTACTGCTGG CACTAAATCC AATTGGAAAT GCCCCACACA

ATTTATCTTC CACTTCATGC TGCTACCATA TGCCTGACGT GGCGGAGCAG AAGCATTCCC

TCCCGTTCTG ATAAATAGTA CTTTGTAAAT ATTTGGAGAC GGGAGCTCTG GTGACAGGGA

ACACGTACAA ACCGGCCTGT TTATCATGTT CCCGATAGAG GCCCTCTTTG ACGTACAGGA

CCCCAAAACA GTCAGGATGC TGTGAATTTC CTTCCATGAA GCCTTGTTCA CAATTAGCAA

CCATTGGAGG AAGCAGGCTG CACTGTCTAC CACAAGTGGC ACTTTCCAAA GAGCACACAT

ATATTGGAGC AAGACATTTT GCTGGCTGAC TGGTGCTGTG TAAGCTGATA AACTGCTATA

TTTATTAAAC TGGCTTTTCT TTGAACACCC CACTCAAGGA AAAAAAAACA CACTTAGGGT

GACATTATTT GGAGATGAAG TCTTTATAGA GATGCTTAAG TTTAAACGAG ACTTTTAAAG

CCGGCTCTAT TCCATTTAAT GAATGGTGTC CCTACAAAGG AAGAAACTGG GACAGAGGTA

TGTACACTTG TGTGTGTGTG AGAGACAACG TGAGGAGCTG AAGAGGAGCA CGTACAAGTC

AGAGAAAGGC TGACCCTTAT TCACACTGAG CAAACCAGTC ATGTGTGGGT CGATAGATGA

GAGTATCCCC CAAGACTCAC ACATTCGAAC GCTTGGTC
```

According to a fifth aspect of the present invention there are provided DNA consisting essentially of a regulatory DNA capable of inducing metastasis from SEQ. ID. NO. 3:

```
AGGACCAGAG TTCACATCCC ATCAAATGGC CCAGAAGGTT TTAATGCTGT CTTTTGGCCC

AGGGCGAAC TGCACACACA TGTGCACATA CACTTACAGA GACACACATT CAGCAGCATA

AGAACACAAT CACAAATAAA AAAAATCTTG AAAAATTTTA AGCTAAAATT GTTAAGAAAT

AACATATATA CAATTTTTCT TTATTTTTTT AAAGATTTAT TTATTTAATG TATATGAGTA
```

-continued

```
CACTGCCTCT CCCTCCAGAC ATAGCAGTAC AGGGCATCGG ATCCCATTAC AGATGGTTGT

GAGCCACCAT GTGGTTTCAC AGATGGTTGT GAGCCACCAT GTGGTTTCAG GAATTGAACT

CAGGACCTTT GGAAGAGCAG TCAGTGCTCT TAACCTCTAA GCCATCTCTC CTGACCCTTA

TATACAATTT TAATGCTACG TACACACAAC TTCTCTTTCC TTTAATGGTT GAGATTTTTG

TCTGGAGAAG TAAGAATAAA GGAGGGAAAG AACATTGCTT TCACATTGCA CCAGTGGGAA

CAGCGTGTTT AAAGTAGGAA TGCCATGAAA TGACTGGCCT GCCTTCTCAT TACTGTTCCT

CCCACTCCTC CTTTTAACTG GAGCTCCTTT ATCTAATTTA TTAGTTTGAC GATACCCAGG

GTTTTCTTCT GTTTTGATCT TTTTAAGACA GAGACTCACC ATATAGCCCT GGCTGGCCTG

AAGCTCACTA TGTAGACCAG TCTGGCCTTG AACTCAAAGG AGATCTATCT GCTTCCTAGT

GCTGGGATTA AAGGCTTGTG CTACCAAGTC TGGTCTGAGG CTTTGGAGCA GCCTCGGTTT

TGGCCTTCTT TAAGGATCTC TAAGCTAGCA GTAAGTAGCC TAGCCATGCT GTTGTAGGAA

GTTGTTCGTT CATCCTGGCT CCAGCACAAA GGCAGTCACT AAACGTCGGC CTCATTTCAT

CAGAGCTGAA TGCAAATTCC TTGTGCTCTT CCTGTGTCCT CCTGGAAC
```

According to a sixth aspect of the present invention there are provided DNA consisting essentially of a regulatory DNA capabel of inducing metastasis from SEQ. ID. NO. 4:

```
AGTTGGGGAC ACAGCTTGCT TGATTAAGAT GTTTCTTGGG AAAAGGAGTT AAGCCTAATG

ATTTCCAATG GAAAGGACTG CTAATTGGGG AGGCAATGTT GCTTAATTGG GACACCTGCG

GGTAATTAAA AGCTCTCTCC CAGTGGCCTT TCCTGTTTTT GGCTCTGGGA GGCGAAGGCA

TTGAGAGGGA TGCAGGCATT CTAAGGGCTG GTTCTTGGTT TCTCCCTTCC CCTCTGTCCA

AACTCAGTGA GGTATCCCTG TCTGTGCTGT CCTTAGAGTG CCGTCCTGAG GCCTTGGTGA

GTTAAGGTCT CTGGATCTGA GCTGCCTCAG GGAAACGCAT GAGCTCATTG GAAAGGGGAG

AACCAGGCAA AGGTGTTGGC TGTGACCTCA GAATTCTGAG GGGCAAAGGT TCAAGGCTAA

CTCTCATTAT AGAGCAAGTT TGAGACTGGC CTGGGAACAA AAATATAAAG TGAGTGAGGT

CATATGACAG CACCTGAGGA GTCCTGTCCC TAGAGATCAT AAGGACCTGG CTGCTGGGGA

CTTGTTGCAG ATGGCACTTT GTGTCGAGAG AGGGGACCTG CCCCAGCATG GGAGGCCCTG

GAAGATCCTC TGGATTAACT GTGAACACTG ATTGCTGCTT TATACCTGGA GTTGTGCTGT

TATCTGGTAC ACATCTGCTG GGTGAATGAG TTCATGGGCT TTATTTCAGT GAGGTATTTA

CCTGAGGAGA AAGAAGGACT GGTGCCACAA AGCACAGCTT TTAAATCTGT GGGTTGTGAC

CCATTATGGA CTATCATAAC TGAGTGCAGG TATCAAGAAT ACTTTAGCAG GTGGTAAAAA

GATTTTTGAA TGCGCAACGA CCAAAACTGA ACTCAAAAAT CAAGCATGGC ATGGATCCTG

GGTGCTCCTG GAAGCACTTG CCTTTACTGC ATTGTGCGAC TTGACGGTAG CCTTGGTTCT

GAATGCACAA CACGTGGGCT TTGGGCTGCA CAGGCCACCA CGCCGTGCCT GAAACACCTC

AGCTCAGGTT TGTGGCTATG TCCTATGACT TGGACTTACT TTTATTGCAC ATATAAATAT

TTTCCTGC
```

According to a seventh aspect of the present invention there are provided DNA consisting essentially of a regulatory DNA capable of inducing metastasis from SEQ. ID. NO. 5:

```
GAGGGGGTGG TGGCACAGTT ATGTTTTTGT AGGAAGGGTT CCATGAACCT CAGCAGAGCT

CGGGTTAGAA ATTTAAAAGC CCTGAGGGGA ATTTTTTTTT TAAATCGCTA TGAATCTGAC

ATGAGAAAAA CAGATCAGAA ACGTTCTTGT GCTTCAGAAA AGGACAAGTG TGTGAGCTAA

CAGACTGCAC ACTGGTGTTC GAGGCACATC TGGATCACAG GAGCGTCAGA TAATGTCCCC

AAAGGTAAAT GCATTTGCTT GCACAGTACC GAGTGTGGTG GGGGGTGCCT ACAGCCCAGC

GGTTCTCAAC CTTCCTGATG CTTCGACCCT TTAATACAGT GCCTCATGCT CTGGTGACCT

CCCCAACCTT AAAATTATTT TTGTTGCTGT TCATAACTGT GATTTTGATA CTGTTATGAA

TTGTAATATA AATAATTTTG AAGAAAGAGG TTTGCCAAGG GTTTGAGAAC TGCTGTTCTA

GCCCCACGTG GATGGTTTTT CGTCATTTGG GGTTTTTATG AGGCAGAGTC TTATGTAGCC

CAGGCTAGCA GCCTAGAATG TGCTACTTAG CTGAGGAATA ACCTTGGAAC TTCTGAGGAC

TGGAGAGACT GGCTTAGTCC TCAAGAAACT GGAAATAGCT GGAGTTTGGC TACTTGTGGG

TTCCTTTTTC TTCAAACCTT TTCTACTCTT TTTCCACCCT GTCGGCCCCC TAACACTAAA

TAAGAAAGAG AAAGGGGAGC ATACAGGGGA AAAGAAACCC CTGAATAACG TCAGTAGTTG

GCAAAGGGGG GTGACATATG TTGTCATTAG ACCACATCCT GGTGATTAAG GGGAGTCAAG

TTCCTTGGGG CAAGTTTGAT CTTTCGTGTA ACGATATCTA ATTTCTTCTC CCTGTTGCTT

CGTCTTTGTG AACAACGACT TGATAACCCA CAATGGACCA TCAACCAACC AACCAACCAT
```

According to an eighth aspect of the present invention there are provided DNA consisting essentially of a regulatory DNA capable of inducing metastasis from SEQ. ID. NO. 6:

```
TTGTCTCTGG TGTTACTTGT TTTCCCATTT CTGACAGTGG TTTGACCTT CTATACGCCT

GTGTGTCAGG AGTGCTGTAG ACCTATTTTC CTGTTTTCTT TCAGCCAGTT ACAGGAACAG

AGTGTTCTAC TGTCAGATGT GTAGCTGTTC CTGTCCACTG ACTTTCAAGC TGTCTCTGTG

TGCAGGAACC AGAAGGGCCT GTCCCTACTT CTACTGGGCC CCTACGCACA GGGGGCCTAG

ATGGTGCTAG GTGTTTTCCT CTAGAGCCTG AAATGTGGGC AGAGAGTAGT CTCCTCTGGT

TTCCTAGGTA TGTCTTCCCC TCTGAAGGTC TAGCTCTCCC TTCCATGGGA TATGGGTGCA

GGGAGCTGTT TGACCAGGTC CTCTCAAATC CGGGTGCAGT CTGGACCGCA GGCTCCTGTA

GCTTGCCTGC TGCAATCTTC CCGCACCCAG AGGCACCCAA GTTTCCTCTT GGGCCAAGGA

TGTGGGCAAA GGTGGGCAGA AGTGGCAATC TCTCCTGCCC TAGCGTCTCA GGATTGCCCT

CACTTCTGGG CAATCCGCTC TCTCTTCCAC AGGGTTTGGG AGCAGGGAGC TGTGGGCCGG

TATCAGGCAA AGGTTTGAGG CAACCAGTTA GAAACTGGAA GTGTCAGGTC CCAGAGGAAT

TTTGCCTTTG TGTGTCCTGA GTCCACCAGG CAGGTCACTT GGAGCAGAAA AATTGGTTTT

CCCCTCGGTC TCAGGCCTGA AGTTGCACCT CAGGGTTGGC TTTCAGCTGT ACCTGTGGAA

AGTATGGTTT TAAAAATCTA AGATAGCTAT CATGCAGCAA GGCTTGTGTA AAATGTCTAT

TTGGTTCCTT TATGACTTAC TTTTGCTGTA CTGAGGATCA AACCTAGGGT CTCAAGCAGT

CATCACAATT CTCTGTCACT GATCCAGCTC CATTTCTATT TTCTTTTGTC CCGCGCGATC

TCTCGCCAGC AAGAAAACAC GCTAGGGACA TACGAATCCT TGCTGCAGCC AAAACTTTTA

TTGAATCTTA AGGAGAAGCC CGCGCACCGG ACTGGCGCGG TTTATATACA CCCTAGCACA

GTGCATCCAC A
```

Detailed examination of their DNA sequences has confirmed that the six Met-DNA's bear little relationship to one another. C6-DNA shows 86% homology to 102 bp of the rat WAP promoter (Nucleic Acids Res. 12 8685–8697 1984) with a novel duplication of 30 nucleotides of this region. All Met-DNAs contain recognition sequences for transcription factors TCF-1 (EMBO J. 10. 123–132, 1991) and HIP1b (Mol.cell. Biol. 10, 653–661, 1990). Moreover all but one contain recognition sequences for CTCF (Oncogene 5, 1743–1753, 1990), HIPla (Mol.Cell.Biol.10, 653–661, 1990), NF-1L6 (EMBO J. 9 457–465, 1990) and regions of potential Z-DNA (Nature 282, 680–686, 1979), with C6-DNA containing a tract of 23 alternating purine-pyrimidine bases. Thus these novel sequences all contain potential regulatory regions for transcription of DNA into mRNA but no known coding or viral-related sequences.

According to an ninth aspect of the present invention there is provided the use of an osteopontin gene as a metastasis inducing transformant.

In one embodiment Met-DNA's, are introduced into a benign rat mammary epithelial cell line Rama 37.

By way of example and to help identify the regulatory function that short stretches of human malignant DNA (precursor to Met-DNA's) may exert on the transfected Rama 37 cells, the mRNA expression of the metastatic transformant rat mammary cell line R37-Ca2-LT1 was compared with its benign parental cell line Rama 37 using subtractive hybridisation techniques. Of the four subtracted clones three corresponded to known rat genes for proteins including osteopontin and one corresponded to a novel rat gene of unknown function. As an example only, transfection of rat osteopontin cDNA into the parental Rama 37 cells produced transformants that induced a high frequency of metastasis compared with vector controls confirming the metastatic capability of the osteopontin gene as shown in Table 2.

TABLE 2

| Transfecting DNA[a] | opn mRNA[b] | No. of rats | % Metastasis[c] |
|---|---|---|---|
| pSV2neo | 1 | 26 | 0 |
| C2-DNA | 2.5[d] | 18 | 33[e] |
| C5-DNA | 1.6[d] | 25 | 12 |
| C6-DNA | 1.6[d] | 18 | 50[e] |
| C9-DNA | 4.4[d] | 23 | 17[e] |
| C12-DNA | 2.8[d] | 13 | 23[e] |
| C20-DNA | 1.8[d] | 13 | 23[e] |
| C9-DNA Lung metastatic line | 16[d] | 24 | 29[e] |
| CMV-1 | 1.1 | 24 | 0 |
| OPN-1 | 6.0[d] | 42 | 55[e] |

These overall results have established a causal relationship between the Met-DNA's and metastasis on the one hand and the over-or underexpression of certain rat genes, at least one of which is novel, that are linked to the metastatic process in this rat system. Controls with DNA's from nonmalignant, nonmetastatic sources as well as the oncogenes Ha-ras-1, Polyoma Large T Antigen and Polyoma Middle T Antigen failed to induce metastasis establishing the specificity of the inductive processes in this system.

At present the most useful indication of whether a breast or other common cancer will metastasise in the future in a patient is whether the primary tumour has already spread to the local lymph nodes. This test only works on a population basis. For example, in breast cancer, there are many examples of patients with no tumour in the lymph nodes at presentation who later die of metastatic disease and of patients with metastatic deposits in the lymph nodes who live a normal life-span. Thus an accurate test of good predictive value for the occurrence of metastases would be important in selecting those patients for vigorous conventional chemotherapeutic treatments without causing the potentially harmful side-effects in those patients who do not need this treatment.

According to a tenth aspect of the present invention there is provided a probe specific to a regulatory DNA capable of inducing metastasis.

By specific is meant hybridises to any target DNA under suitable salt and temperature conditions to allow detection of identical or related DNA molecules.

Preferably the probe is provided as part of a kit which may additionally comprise one or more of the following: a colour indicator; an oligonucleotide primer; materials for gel analysis, and/or materials for DNA transfer or hybridisation.

The Met-DNA sequences may be detected in tumour or biopsy specimens by standard Southern blotting, PCR-based or in-situ techniques to identify those patients at risk from metastatic disease. Physical methods of detection based on imaging techniques may also be possible. Expression of metastasis—inducing genes may be detected by standard mRNA hybridisation PCR amplification or by antibodies specific for the gene-product.

According to a eleventh aspect of the present invention there is provided a medicament adapted to target a regulatory DNA capable of inducing metastasis as claimed in any of claims 7 to 13.

In one embodiment such Met-DNA's, metastasis-inducing genes or fragments thereof, could be targeted in the cancer cells to excise or block their function using synthetic oligonucleotides based on a knowledge of the sequence of the Met-DNA's, metastasis-inducing genes or fragments thereof, of the invention.

In another embodiment such Met-DNA's, metastasis-inducing genes or fragments thereof, may be targeted for treatment using standard antibody and antisense mRNA/ribozyme techniques for detection and for destruction, respectively.

What is claimed is:

1. A method of screening and recovering a regulatory DNA which is not expressed as an mRNA but is capable of inducing metastasis comprising the steps of:

i. transferring fragments of human DNA of less than 1.5 kb in length, said fragments having been tagged at both ends with double-stranded synthetic oligonucleotides that provide restriction enzyme and unique primer sites, from malignant, metastatic cancer cells, into a rat or mouse cell line that produces only benign, non-metastasizing tumours when injected into a syngeneic rat or mouse, thereby producing transformed cells;

ii. injecting the transformed cells into syngeneic rats or mice;

iii. selecting those rats or mice in which metastasizing tumours have been identified; and iv. recovering the regulatory DNA capable of inducing metastasis therefrom.

2. The method of claim 1 wherein said fragments of human DNA are between 1.3 and 1.5 kb in length.

3. A method as in claim 1, in which the cell line that produces only benign non-metastasizing tumors is a rat mammary epithelial cell line.

4. A method as in claim 1 wherein the fragments of human DNA are tagged.

5. The method of claim 4 wherein the fragments are tagged with a double-stranded synthetic oligonucleotide, one strand whose sequence is SEQ. ID. No. 7 and the other strand whose sequence is SEQ. ID. NO. 8.

6. A regulatory DNA which is not expressed as an mRNA but is capable of inducing metastasis, said regulatory DNA consisting essentially of a human DNA fragment of less than 1.5 kb in length and comprising the sequence of SEQ. ID. NO. 4, obtained from a malignant, metastasis cancer cell.

7. DNA consisting essentially of a regulatory DNA which is not expressed as an mRNA but is capable of inducing metastasis and has the sequence of SEQ. ID. NO. 4.

8. A method as in claim 2, in which the cell line that produces only benign non-metastasizing tumors is a rat mammary epithelial cell line.

* * * * *